(12) United States Patent
Leach et al.

(10) Patent No.: US 8,299,119 B2
(45) Date of Patent: Oct. 30, 2012

(54) BIOLOGICALLY ACTIVE COMPOUNDS

(75) Inventors: David Leach, New South Wales (AU);
Lesley Stevenson, Auckland (NZ);
Brigitte Gabriel, Innsbruck (AT);
Karren Beattie, New South Wales (AU)

(73) Assignee: Bio-Active Export Pty. Ltd., Melbourne Victoria (AU)

( * ) Notice: Subject to any disclaimer, the term of this patent is extended or adjusted under 35 U.S.C. 154(b) by 730 days.

(21) Appl. No.: 12/085,741

(22) PCT Filed: Nov. 29, 2006

(86) PCT No.: PCT/AU2006/001812
§ 371 (c)(1),
(2), (4) Date: Mar. 18, 2009

(87) PCT Pub. No.: WO2007/062468
PCT Pub. Date: Jun. 7, 2007

(65) Prior Publication Data
US 2009/0221517 A1 Sep. 3, 2009

(30) Foreign Application Priority Data
Nov. 29, 2005 (AU) ................................. 2005906666

(51) Int. Cl.
*A01N 37/10* (2006.01)
*A61K 31/235* (2006.01)
*C07C 69/76* (2006.01)
(52) U.S. Cl. ........................................ 514/533; 560/60
(58) Field of Classification Search ........................ None
See application file for complete search history.

(56) References Cited

FOREIGN PATENT DOCUMENTS
| CN | 1569868 | 1/2005 |
| CN | 1687098 | 10/2005 |
| WO | WO 98/32454 | 7/1998 |

OTHER PUBLICATIONS

Database WPI Week 200577, Thomson Scientific, London, GB; AN, 2005-749421, XP002586304.
Database WPI Week 200621, Thomson Scientific, London, GB; AN, 2006-194930, XP002586305.

*Primary Examiner* — Traviss C McIntosh, III
(74) *Attorney, Agent, or Firm* — Gordon & Rees LLP; Laurie A. Axford

(57) ABSTRACT

Compounds having useful biological activity, particularly antioxidant and anti-inflammatory activity, derived from *Centipeda cunninghamii*, and biologically active derivatives thereof, pharmaceutical compositions comprising these compounds, and prophylactic and therapeutic use of the compounds.

11 Claims, 9 Drawing Sheets

HPLC Analysis of *C. cunninghamii* extract (CS) CI (10-95)

HPLC Analysis of *C. cunninghamii* BG (2-35)

TIC and EICs for P6 and P4 from Fresh *C. cunninghamii* Extract

A

B

MS for P4 (A; m/z 495) and Aglycone (m/z 333) and P6 (B m/z 546).

The MS Data for P4 Glycoside and Aglycone.

Isolation scheme for anti-inflammatory and anti-oxidant compounds from *C. cunninghamii*.

Compounds isolated from *C. cunninghamii*.

BIOLOGICALLY ACTIVE COMPOUNDS

FIELD OF THE INVENTION

This invention relates to compounds having useful biological activity; more specifically to compounds having antioxidant and anti-inflammatory activity. In particular, this invention relates to such biologically active compounds derived from *Centipeda cunninghamii*, and biologically active derivatives thereof.

BACKGROUND OF THE INVENTION

The reference to any prior art in this specification is not, and should not be taken as, an acknowledgment or any form of suggestion that that prior art forms part of the common general knowledge in Australia.

There is at the present time a significant medical need for new anti-inflammatory and anti-arthritic drugs with reduced side effects and prolonged in vivo activity and in particular for compounds which will moderate the progress of the arthropathies. Plants and other living cells offer a vast reservoir of compounds which have pharmacological effects on humans. Natural products have frequently been the source of effective drugs and lately there has been an increased interest in the analysis of these natural products, especially where a clinical benefit is claimed.

*Centipeda cunninghamii* and related plant species have been used by the Aboriginal people of Australia for many generations in the treatment and prevention of many ailments. *C. cunninghamii* is commonly known as Gukwonderuk, koona puturku, sneezeweed, old man weed or scent wood. *C. cunninghamii* is known to grow primarily in the lower temperate regions of south-eastern Australia. It is commonly found along stream banks and in the back wash of rivers or streams where the water is stagnant.

Traditionally, *C. cunninghamii* has been used by the Aboriginal people as an aqueous infusion or tea, which has either been taken orally or used directly on the skin. Although *C. cunninghamii* has been used by the Aboriginal people there is little known about this plant and the active component(s) responsible for its various properties.

International Patent Application No. PCT/AU98/00031 (WO 98/32454), the content of which is incorporated herein by reference, discloses compositions comprising an extract from plants in the genus *Centipeda*, more particularly an aqueous alcoholic extract of *C. cunninghamii* or a related *Centipeda* species useful in the effective treatment and prophylaxis of many types of medical problems as well as for cosmetic applications.

SUMMARY OF THE INVENTION

As described above, the present invention relates to biologically active compounds derived from *Centipeda cunninghamii*, and biologically active derivatives thereof.

In one aspect, the present invention provides a compound of Formula I:

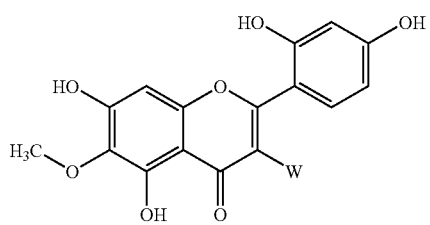

or Formula II:

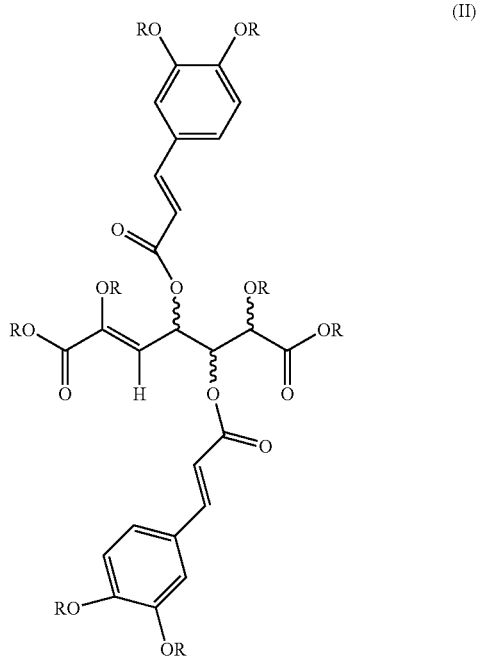

wherein W is a monosaccharide group selected from pentose and hexose sugars in pyranose or furanose form, a substituted monosaccharide group in which one or more of the —OH groups of a said pentose or hexose sugar is replaced by an —$OR_1$ group or a disaccharide group comprising two of said monosaccharide or substituted monosaccharide groups linked by a glycosidic bond;

wherein each R, which may be same or different, is selected from the group consisting of hydrogen and $R_1$; and each $R_1$, which may be the same or different, is selected from the group consisting of substituted or unsubstituted alkyl, substituted or unsubstituted cycloalkyl, substituted or unsubstituted cycloalkylalkyl, substituted or unsubstituted aryl, substituted or unsubstituted arylalkyl, a protecting group, —C(O)—$R^a$, —C(O)O—$R^a$, —C(O)$NR^aR^a$—, —S(O)$_n$—$R^a$ and —S(O)$_n$—$NR^aR^a$ (wherein n represents 1 or 2, and $R^a$ is selected from the group consisting of hydrogen and substituted or unsubstituted alkyl); and their pharmaceutically acceptable salts.

Preferably in the compounds of Formulae I and II, $R_1$ is selected from hydrogen and alkyl.

In another aspect, the present invention also provides a compound selected from:
(i) 2',4',5,7-tetrahydroxy-6-methoxyflavone-3-O-β-glucopyranoside (Compound 1)
(ii) 4ξ,5ξ-Di-O-caffeoyl-2,6ξ-dihydroxyhept-2-en-1,7-dioic acid (Compound 2)
(iii) 4ξ,5ξ-Di-O-caffeoyl-2,6ξ-dihydroxyhept-2-en-1,7-dioic acid-7-methyl ester (Compound 8)
(iv) 4ξ,5ξ-Di-O-caffeoyl-2,6ξ-dihydroxyhept-2-en-1,7-dioic acid-1-methyl ester (Compound 9)
(v) 4ξ,5ξ-Di-O-caffeoyl-2,6ξ-dihydroxyhept-2-en-1,7-dioic acid-dimethyl ester (Compound 10)

in substantially purified form, and pharmaceutically acceptable salts thereof.

In a further aspect, the present invention provides a method of antioxidant or anti-inflammatory treatment of a human or other mammal, which comprises administration to said human or other mammal of a therapeutically effective amount of a compound of Formula I or Formula II above, or a pharmaceutically acceptable salt thereof.

In a particular embodiment, the invention provides a method of antioxidant or anti-inflammatory treatment of a human or other mammal, which comprises administration to said human or other mammal of a therapeutically effective amount of a compound selected from the group consisting of Compound 1, Compound 2, Compound 8, Compound 9 and Compound 10 above, or a pharmaceutically acceptable salt thereof.

In yet another aspect, the present invention provides a pharmaceutical composition for antioxidant or anti-inflammatory treatment of a human or other mammal which comprises a compound of Formula I or Formula II above, or a pharmaceutically acceptable salt thereof, together with one or more pharmaceutically acceptable carriers and/or diluents.

In a particular embodiment, the invention provides a method of antioxidant or anti-inflammatory treatment of a human or other mammal, which comprises administration to said human or other mammal of a therapeutically effective amount of a compound selected from the group consisting of Compound 1, Compound 2, Compound 8, Compound 9 and Compound 10 above, or a pharmaceutically acceptable salt thereof, together with one or more pharmaceutically acceptable carriers and/or diluents.

The present invention also provides the use of a compound of Formula I or Formula II above, or a pharmaceutically acceptable salt thereof, in the manufacture of a composition for antioxidant or anti-inflammatory treatment of a human or other mammal.

In a particular embodiment, the present invention provides the use of a compound selected from the group consisting of Compound 1, Compound 2, Compound 8, Compound 9 and Compound 10 above, or a pharmaceutically acceptable salt thereof, in the manufacture of a composition for antioxidant or anti-inflammatory treatment of a human or other mammal.

Throughout this specification and the claims which follow, unless the context requires otherwise, the word "comprise", and or variations such as "comprises" or "comprising", will be understood to imply the inclusion of a stated integer or step or group of integers or steps but not the exclusion of any other integer or step or group of integers or steps.

Reference to any prior art in this specification is not, and should not be taken as, an acknowledgment or any form of suggestion that this prior art forms part of the common general knowledge in any country.

DETAILED DESCRIPTION OF THE INVENTION

Figure 1:
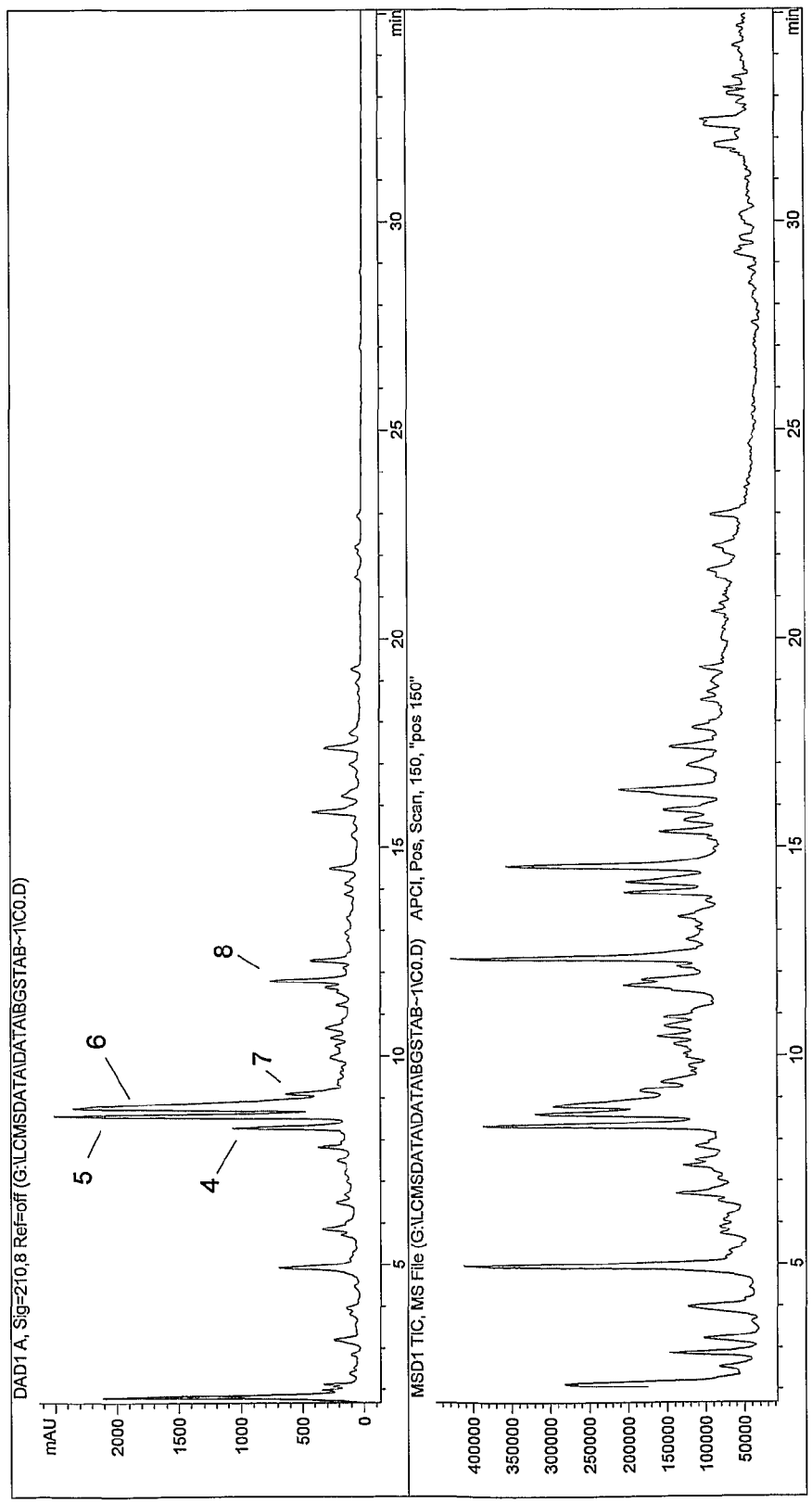
FIG. 1: HPLC analysis of *C. cunninghamii* extract (CS) CI(10-95).

With reference to the monosaccharide or disaccharide group which is linked to the flavone skeleton of FIG. I, preferred monosaccharide groups include groups derived from the pentose sugars D-ribose, D-arabinose and D-xylose and the hexose sugars D-glucose, D-mannose, D-galactose and D-fructose. Preferred disaccharide groups include groups derived from sucrose, lactose and maltose. Particularly preferred monosaccharide groups are β-D-glucopyranoside groups of Formula III:

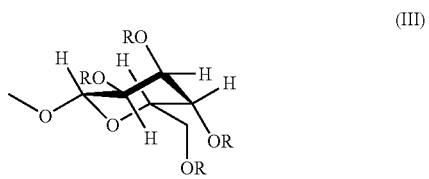

(III)

wherein R is defined above.

In Formula I and Formula II herein:

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronaphthyl, ademantyl and norbornyl groups bridged cyclic group or sprirobicyclic groups, e.g. spiro (4,4) non-2-yl.

The term "cycloalkylalkyl" refers to a cycloalkyl group as defined above directly attached to alkyl group which is then attached to the main structure at any carbon from alkyl group that results in the creation of a stable structure such as cyclopropylmethyl, cyclobutylethyl, cyclopentylethyl, and the like.

The term "alkoxy" refers to an alkyl group as defined above attached via an oxygen linkage to the rest of the molecule, such as —$OCH_3$, —$OC_2H_5$ and the like.

The term "aryl" refers to aromatic radicals having in the range of 6 up to 14 carbon atoms such as phenyl, naphthyl, tetrahydronaphthyl, indanyl, biphenyl and the like.

The term "arylalkyl" refers to an aryl group as defined above directly bonded to an alkyl group as defined above, e.g., —$CH_2C_6H_5$, —$C_2H_5C_6H_5$ and the like.

Substituents in the "substituted alkyl", "substituted cycloalkyl", "substituted cycloalkylalkyl", "substituted arylalkyl" or "substituted aryl" groups may be the same or different, and may be selected from groups such as hydrogen, hydroxy, halogen, carboxyl, cyano, nitro, oxo (=O), thio (=S), substituted or unsubstituted alkyl, substituted or unsubstituted alkoxy, substituted or unsubstituted aryl, substituted or unsubstituted arylalkyl, substituted or unsubstituted cycloalkenyl, substituted or unsubstituted amino, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—N($R^x$)$R^y$, —$NR^xC(O)OR^y$, —$NR^xR^y$, —$NR^xC(O)R^y$, —$NR^xC(S)R^y$, —$NR^xC(S)NR^yR^z$, —$SONR^xR^y$—, —$SO_2NR^xR^y$, —$OR^x$, —$OR^xC(O)NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, and —$ONO_2$, wherein $R^x$, $R^y$ and $R^z$ in each of the above groups can be hydrogen atom, substituted or unsubstituted alkyl, substituted or unsubstituted alkoxy, substituted or unsubstituted aryl, substituted or unsubstituted arylalkyl, substituted or unsubstituted cycloalkyl, or substituted or unsubstituted amino.

Pharmaceutically acceptable salts include salts derived from inorganic bases such as Li, Na, K, Ca, Mg, Fe, Cu, Zn, Mn; salts of organic bases such as N,N'-diacetylethylenediamine, glucamine, triethylamine, choline, dicyclohexylamine, metformin, benzylamine, trialkylamine, thiamine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine and the like; quaternary ammonium salts of the compounds of invention with alkyl halides, alkyl sulphats like MeI, $(Me)_2SO_4$ and the like, non-natural amino acids such as D-isomers or substituted amino acids; guanidine, substituted guanidine wherein the substituents are selected from nitro, amino, alkyl, alkenyl, alkynyl, ammonium or substituted ammonium salts and aluminium salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, ketoglutarates and the like.

As used herein, "treating" or "treatment" of a state, disorder or condition includes:
(1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition;
(2) inhibiting the state, disorder or condition, i.e., arresting or reducing the development of the disease or at least one clinical or subclinical symptom thereof; or
(3) relieving the disease, i.e., causing regression of the state, disorder or condition or at least one of its clinical or subclinical symptoms.

The benefit to a subject to be treated is either statistically significant or at least perceptible to the patient or to the physician.

A "therapeutically effective amount" means the amount of a compound that, when administered to a human or other mammal for treating a state, disorder or condition, is sufficient to effect such treatment. The "therapeutically effective amount" will vary depending on the compound, the disease and its severity and the age, weight, physical condition and responsiveness of the mammal to be treated.

(1) Compounds.

In one aspect, the present invention provides an isolated compound selected from the group consisting of Compound 1, Compound 2, Compound 8, Compound 9 and Compound 10 above, in substantially purified form, or a pharmaceutically acceptable salt thereof. These compounds may be isolated from plant material and extracts of *C. cunninghamii* by methods described in the Examples herein.

The term "isolated" means that the compound is substantially or essentially freed from components that normally accompany it in its native state in *C. cunninghamii* by at least one purification or other processing step. Such a compound may also be described as substantially pure. The term "substantially pure" as used herein describes a compound that has been separated from components that naturally accompany it. Typically, a compound is substantially pure when at least 50%, more preferably at least 70% or 80%, even more preferably at least 90%, and most preferably at least 95% or even 99% of the total material (by volume, by wet or dry weight, or by mole percent or mole fraction) is the compound of interest. Purity can be measured by any appropriate method, for example by chromatography, gel electrophoresis or HPLC analysis.

In another aspect, the present invention provides a compound of Formula I or Formula II, or a pharmaceutically acceptable salt thereof.

Compounds of Formula I or Formula II may be synthesised from the compounds isolated from plant material and extracts of *C. cunninghamii*, by methods which are well known to skilled chemists in this field.

(2) Formulations

The present invention also extends to pharmaceutical compositions for antioxidant or anti-inflammatory treatment of a human or other mammal which comprise a compound of Formula I or Formula II as described above, or a pharmaceutically acceptable salt thereof, together with one or more pharmaceutically acceptable carriers and/or diluents.

The invention also extends to the use of a compound of Formula I or Formula II as described above, or a pharmaceutically acceptable salt thereof, in the manufacture of a composition for antioxidant or anti-inflammatory treatment of a human or other mammal.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate such compositions in dosage unit form for ease of administration and uniformity of dosage. Dosage unit form as used herein refers to physically discrete units suited as unitary dosages for the human or other mammalian subjects to be treated; each unit contains a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

(3) Administration

The present invention further extends to the methods for antioxidant or anti-inflammatory treatment of a human or other mammal by administering a therapeutically effective amount of a compound of Formula I or Formula II as described above or a pharmaceutically acceptable salt thereof.

Preferably, this treatment is administered to a human or other mammal in need of therapeutic or prophylactic treatment for a disease condition or potential disease condition. Most preferably, the treatment is treatment of a human.

Antioxidants are attracting considerable research interest with respect to their actual or potential role in the prevention or treatment of a wide range of mostly chronic conditions, including cardiovascular diseases (incl. atherosclerosis), diabetes, Alzheimer disease, systemic inflammatory disorders and cancer. As used herein, the term "antioxidant treatment" relates to prevention or treatment of disease conditions such as those described where compounds with antioxidant activity have an actual or potential role in prevention or treatment of the condition.

The term "anti-inflammatory treatment" as used herein relates to treatment of inflammatory conditions in general, including arthritic conditions having an inflammatory component such as osteoarthritis and rheumatoid arthritis, as well as treatment of other disease conditions involving inflammation such as multiple sclerosis.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include parenteral (e.g. subcutaneous, intramuscular and intravenous), oral, rectal, topical, nasal and transdermal routes.

The active component may conveniently be presented in unit dosage form and suitable compositions for administration may be prepared by any of the methods well known in the art of pharmacy. Such methods include the step of bringing the active component into association with a carrier and/or diluent which may include one or more accessory ingredients. In general, the compositions are prepared by uniformly and intimately bringing the active component into association with a liquid carrier, a finely divided solid carrier, or both, and then, if necessary, shaping the product.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Other delivery systems can include sustained release delivery systems. Preferred sustained release delivery systems are those which can provide for release of the active component of the invention in sustained release pellets or capsules. Many types of sustained release delivery systems are available; these include, but are not limited to: (a) erosional systems in which the active component is contained within a matrix, and (b) diffusional systems in which the active component permeates at a controlled rate through a polymer.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01-1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

Preparation of *C. cunninghamii* Extracts.
1.2.1. Materials

The analytical balance was from Mettler Toledo (AG 285), the grinder was a Kika (MF10 basic) with 4000 rpm. The sonicator used was from Ultrasonic and the centrifuge from Hettich Universal (16A). The rotavapor was a Buchi R-114. Milli Q water was obtained by filtration with 0.22 µm Millipore. The extraction solvent was ethanol and was purchased from Aldrich (HPLC grade) and DMSO (dimethylsulphoxide) SIGMA D-5879. The LCMS instrument used was an Agilent 1100 Series HPLC with a Phenomenex "aqua" C18 5µ 150×4.6 mm HPLC column. The column temperature was 40° C. The UV data was obtained by an Agilent 1100 series Diode Array UV/VIS Detector and the mass spectra by the Hewlett Packard 1100 Series Mass Selective Detector, The mass spectrometer conditions were drying gas flow: 5 L/min, nebulizer pressure at 60 psig, vaporizer temperature: at 400° C., mass range at 100-1350 amu, Fragmentor voltage at 150 V, mode at scan and the polarity was positive. The HPLC solvents were acetonitrile (HPLC grade) purchased from LAB-SCAN (C-3502 U) and Milli Q water. For preparative purposes the Gilson HPLC system with 306 pump, a UV/VIS-155 detector, an Alltima $C_{18}$ column (22×150 mm, 5 µm) and an attached FC 204 fraction collector was used. To dry the samples a Christ Alpha 2-4 and a Christ Alpha RVC were used. NMR spectra were acquired on a Bruker AVANCE DRX500 ($^1$H, 500.13 MHz; $^{13}$C, 125.77 MHz) spectrometer.
1.2.2. Extract Preparation The entire *Centipeda cunninghamii* plant was harvested for extraction. Samples of plant material were deposited in the Medicinal Plant Herbarium at Southern Cross University (NCM-D-04-113 and NCM-D-05-008). The plant material was chopped and dried for storage until needed. It was then ground using the Kika grinder to get a sufficiently small particle size to promote efficient contact with the solvent. One part plant material was mixed with five parts of 45/55 ethanol/water as a solvent. Two different extraction procedures were compared; maceration, with or without sonication. The resulting extract was dark reddish-brown. The dried extract was dark brown and hygroscopic.

1.2.2.1. Extracts for LCMS

An extract of ratio 1:5 (plant material:solvent) was prepared. Two vials each with 1 g of plant material were prepared and 5 mL of 45% ethanol added. One vial was sonicated for 10 minutes (CS) and one not (C). Both were steeped for 24 hours. The extract was centrifuged at 3000 rpm for 10 minutes and the clear supernatant used to run a profile on the LCMS (see FIG. 1). A larger extract was made for preparative HPLC using the same extraction technique.

1.2.2.2. Extracts for Pharmacology

The same extraction procedure was used as above. The solution obtained was taken to dryness on the rotary evaporator under vacuum. See Table 1 for extraction yield.

TABLE 1

Extraction Yield of *C. cunninghamii*

| Extract Solvent | Yield CS (g) | Yield C (g) |
|---|---|---|
| 45% ethanol | 0.0614 | 0.0776 |

The dried extracts were dissolved using acetone and transferred to a 25 mL screw top vial and dried with $N_2$. The dried extracts were reconstituted for pharmacological assays. For the ORAC (oxygen radical absorbance capacity) assay 75% ethanol was used as a solvent. For the other assays 100% DMSO (dimethyl sulphoxide) was used instead of ethanol. Different concentrations of *C. cunninghamii* extract were prepared and stored in the freezer at −20° C.

1.2.3. Identification and Isolation of Compounds with HPLC

To identify and quantify the constituents of the extracts profiles were generated using Liquid Chromatography/Mass Spectrometry (LCMS). The stationary phase was a RP-C18 column consisting of silica based packing with a covalently bound octadecyl ligand. The mobile phase was water and acetonitrile (ACN) both containing 0.05% trifluoroacetic acid (TFA).

The HPLC had an UV detector, which measured the ability of a compound to absorb light at a specific wavelength. The instrument used had a Diode Array detector (DAD) which scanned wavelengths from 190 nm to 800 nm for each peak. The data were displayed at 210 nm, 280 nm and 360 nm.

A Mass Selective (MS) detector was attached, which gave information on the mass of compounds and fragmentation patterns. The molecule was ionized using an APCI (atmospheric pressure chemical ionization) spray chamber and then passed through a mass selective detector where the ion current was detected.

1.2.3.1. HPLC Methods

Three different HPLC methods were used:

CI (10-95)

A gradient ranging from 90% to 5% water with ACN over 30 minutes was used for the preliminary profiles. Flow rate was 1 mL/min, the injection volume 10 μL and stop time 45 minutes.

CI (10-95) M

A gradient ranging from 90% to 5% water with ACN over 18 minutes was used for the preliminary profiles. Flow rate was 1 mL/min, the injection volume 10 μL and stop time 25 minutes.

BG (2-35)

A gradient ranging from 98% to 65% water with ACN over 20 minutes was used. Stop time was 40 minutes. At the LCMS the flow rate was 1 mL/min and the injection volume was 10 μL. On the preparative HPLC the flow rate was 25 mL/min and injection volume 1 mL.

LCMS profiles of the different extracts of *C. cunninghamii* were made. The CI (10-95) method was used. The HPLC trace at 210 nm and the Total Ion Chromatogram (TIC) are shown in FIG. 1. There was no difference in the HPLC traces between the sonicated and the non-sonicated extract.

TABLE 2

Retention Time and Mass of the Major Peaks in *C. cunninghamii* CI (10-95)

| Peak Nr. | Retention Time (min) | Mass $[M + 1]^+$ m/z |
|---|---|---|
| 4 | 8.2 | 495 |
| 5 | 8.5 | 499 |
| 6 | 8.7 | 546 |
| 8 | 11.6 | 333 |

Figure 2:
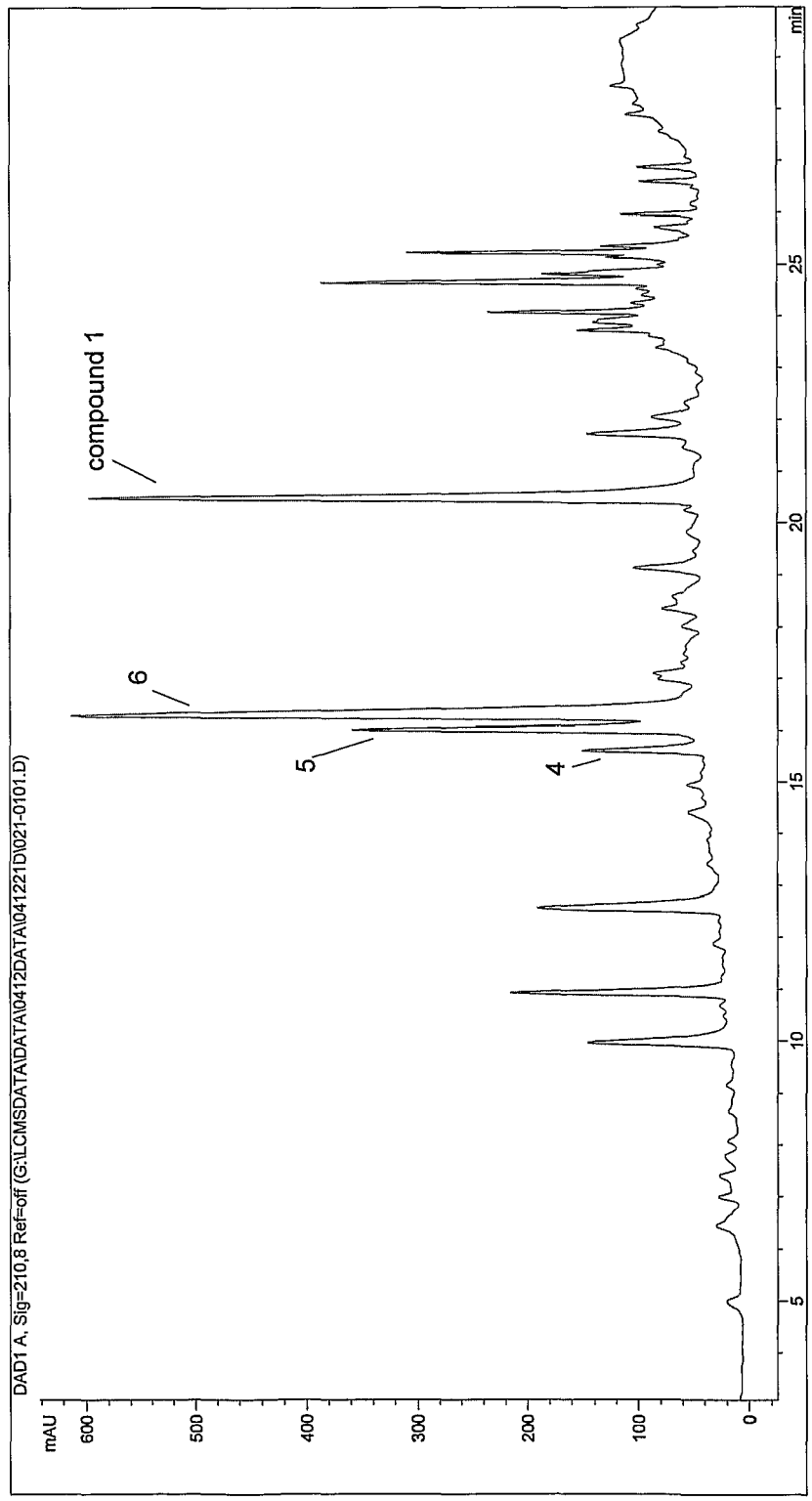
FIG. 2: HPLC analysis of *C. cunninghamii* BG (2-35).

The crude ethanol extract was separated by preparative HPLC to obtain pure compounds for identification by NMR. To prepare enough material preparative columns were utilized. The prep-column had column dimensions of 22×150 mm which was designed to facilitate large volume injections into the HPLC system. One gram extract was dissolved in 10 mL 50:50 water and ACN. The injection volume was 1 mL which gave the total amount of 100 mg extract on the column. The system used was a Gilson HPLC system which had an automatic fraction collector attached which was programmed to collect 30 second fractions. 40 fractions were collected per run. As the main peaks of interest were peak 4 and 6 a new method was developed which showed a better separation in this particular area. The method was BG (2-35) and the HPLC trace is shown in FIG. 2.

To obtain enough material for the NMR two runs were performed and after purity checks on the LCMS the fractions were combined. The gradient method used on the LCMS was CI (10-95) M.

To collect peak 4 and peak 6 more runs were made with the same method. After purity checks on the LCMS fraction 8 was found to be pure and identified as peak 6 with $[M+1]^+$ of 546. Fraction 3 was identified as peak 4 with $[M+1]^+$ of 495. The fractions were taken to dryness on the rotary evaporator and then further dried on the RVC. The yield of peak 6 was 13.0 mg and of peak 4 12.1 mg.

EXAMPLE 2

Active Constituents of *C. cunninghamii*.

Fresh ethanolic extracts of *C. cunninghamii* were subjected to bioassay guided fractionation using preparative HPLC on C18 as described in Example 1. One minute fractions were cut and pooled according to the HPLC profile using the detector response at 210 nm. The raw data is summarised below.

TABLE 3

Description of Samples

| Sample | Description |
|---|---|
| E1 | Fractions 1-6 |
| E2 | Fractions 7-12 |
| E3 | Fractions 13-16 |

TABLE 3-continued

Description of Samples

| Sample | Description |
|--------|-------------|
| E4 | Fractions 17-24 |
| E5 | Fractions 25-29 |
| E6 | Fractions 30-35 |
| E7 | Fractions 36-40 |
| P4 | Purified Compound 1 |
| P6 | Purified Compound 2 |

EXAMPLE 3

Identification of Active Constituents

Two novel compounds with confirmed biological activity were isolated and identified in the fresh *C. cunninghamii* extract and these were identified as P4 (Compound 1) and P6 (Compound 2) based on NMR and MS data.

Figure 3:
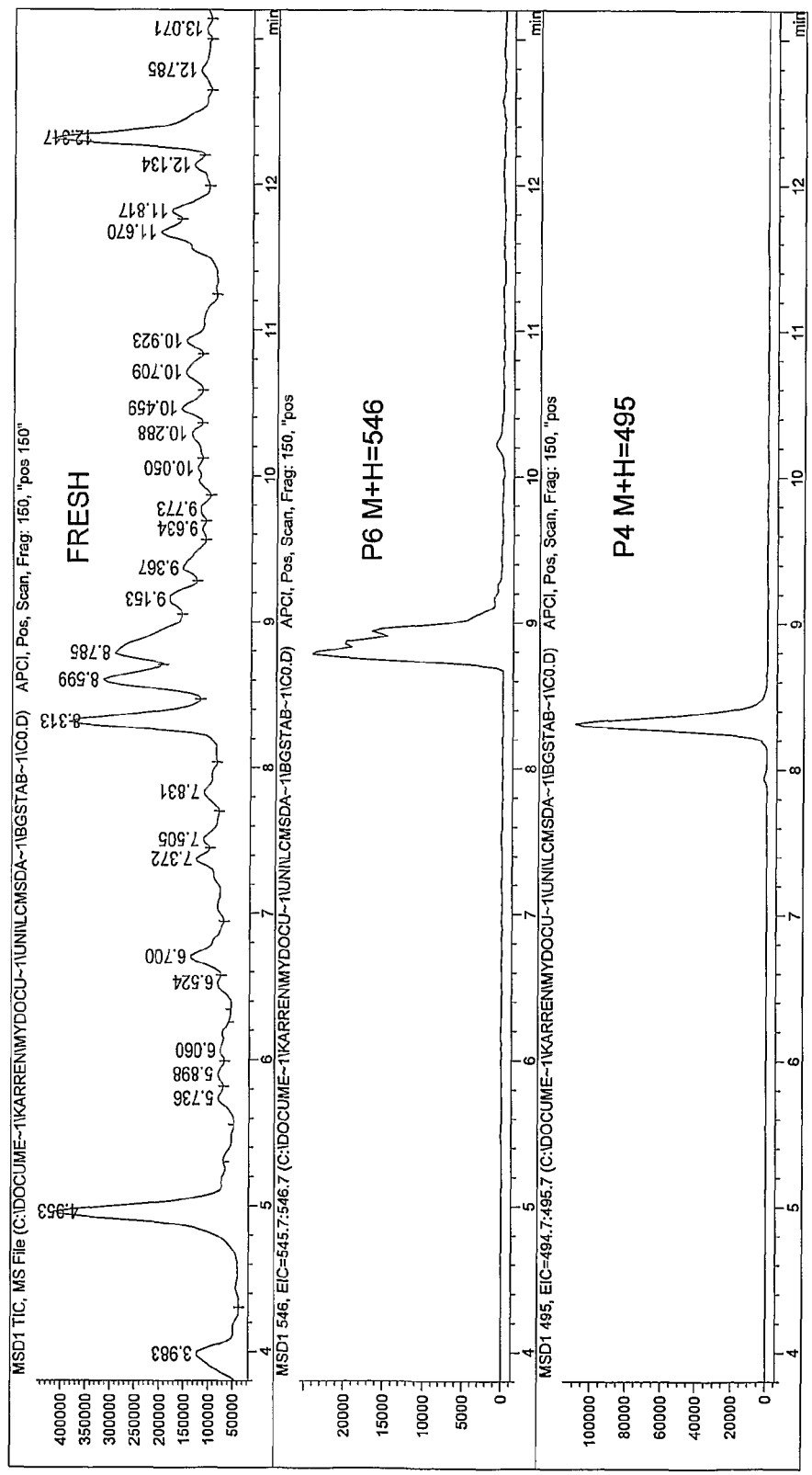
FIG. 3: TIC and EICs for P6 and P4 from fresh *C. cunninghamii* Extract.
Figure 4:
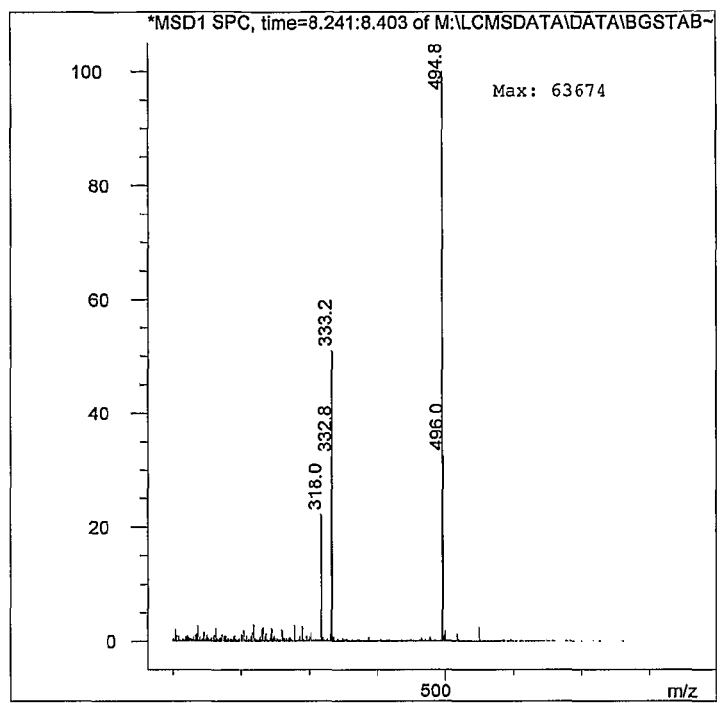
FIG. 4: (A) MS for P4 (m/z 495) and (B) Aglycone (m/z 333) and P6 (m/z 546).
Figure 4:
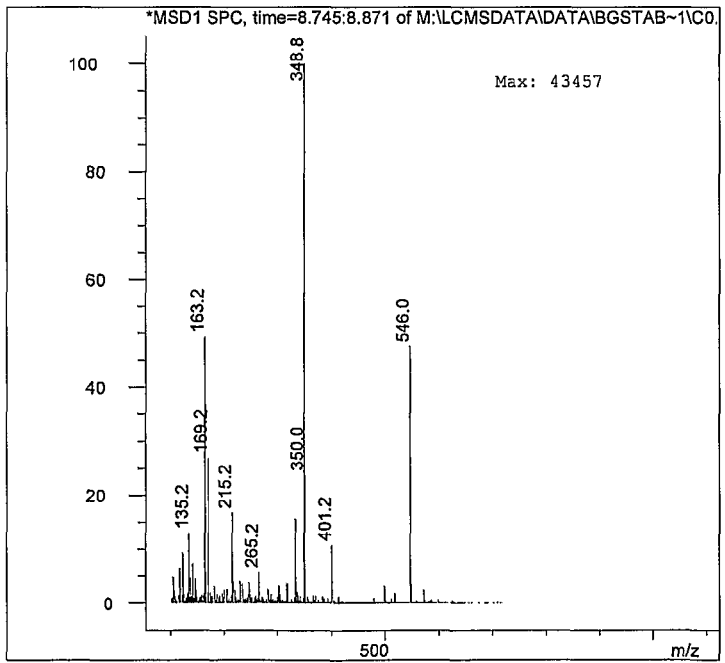
Figure 5:
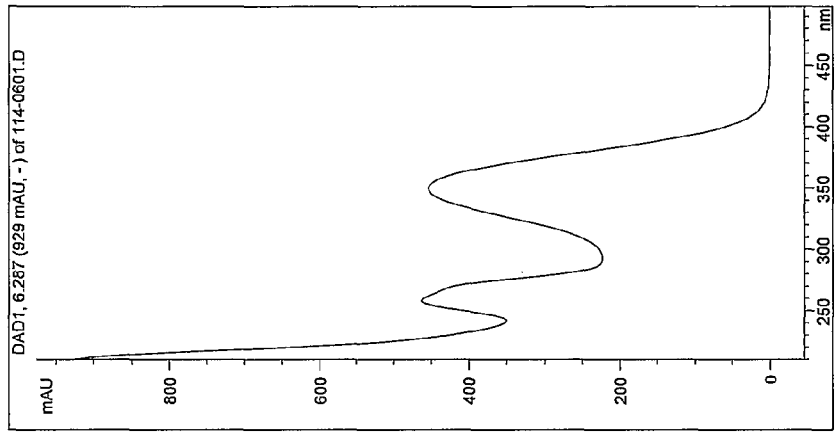
FIG. 5: UV and MS spectra for P4.
Figure 5:
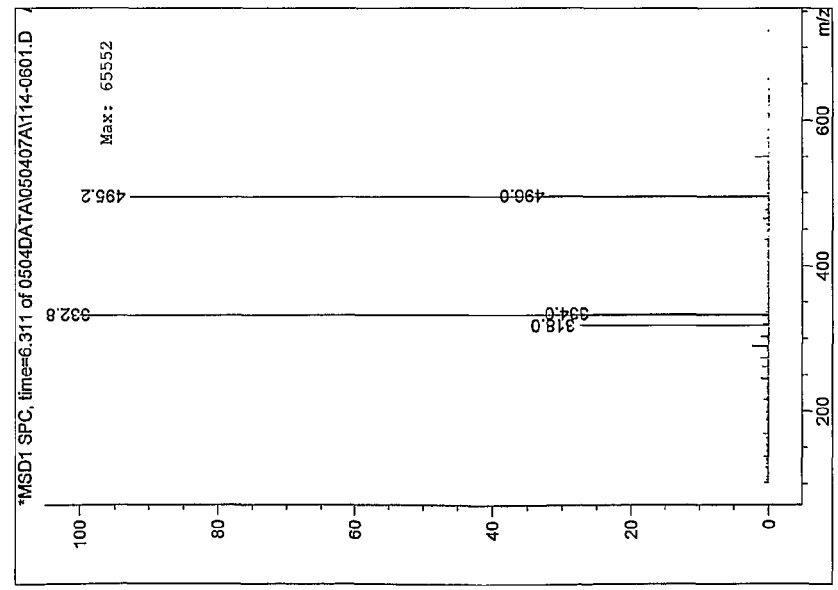

Compound 1 or P4 elutes at 8.3 minutes and is characterised by the EIC (Extracted Ion Chromatogram, FIG. 3) using m/z 495 (the parent ion plus H, M+H or M+1) as shown in FIG. 4A. Chemical data for P4 are set out below, and NMR spectral data are set out in Table 4. UV and MS spectra for P4 are shown in FIG. 5.

| | |
|---|---|
| Chemical Name: | 5,7,2',4'-tetrahydroxy-6-methoxyflavone-3-O-β-glucopyranoside |
| Molecular Formula: | $C_{22}H_{22}O_{13}$ |
| Molecular Weight: | 494 |
| Optical Rotation, $[\alpha]_D$: | −14.5043 (Conc.: 0.2300 in methanol at 23.3° C.) |
| Chemical Structure: | 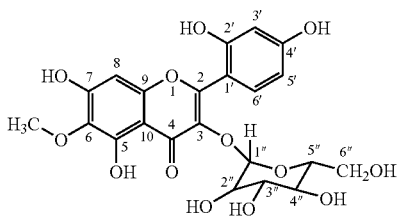 |

TABLE 4

$^1$H (500.13 MHz) and $^{13}$C (125.77 MHz) NMR spectral data for P4 in methanol-$d_4$.

| Position C/H | Chemical Shift, ppm | |
|---|---|---|
| | $^1$H$^a$ | $^{13}$C |
| 1 | — | — |
| 2 | — | 146.1 |
| 3 | — | 135.5 |
| 4 | — | 179.9 |
| 5 | — | 153.9 |
| 6 | — | 132.9 |
| 7 | — | 154.0 |
| 8 | 6.52 s | 95.1 |
| 9 | — | 159.0 |
| 10 | — | 106.3 |
| 1' | — | 123.3 |
| 2' | — | 159.4 |
| 3' | 7.71 d (2.2) | 117.7 |
| 4' | — | 150.0 |
| 5' | 7.59 dd (2.2, 8.5) | 123.4 |
| 6' | 6.87 d (8.5) | 116.2 |
| 1" | 5.26 d (7.6) | 104.4 |
| 2" | 3.49 dd (7.6, 9.1) | 75.9 |
| 3" | 3.43 dd (8.7, 9.1) | 78.3 |
| 4" | 3.35 dd (8.7, 9.6) | 71.4 |
| 5" | 3.22 ddd (2.4, 5.4, 9.6) | 78.5 |
| 6" | 3.70 dd (2.4, 11.9) | 62.7 |
| | 3.57 dd (5.4, 11.9) | |
| —OCH$_3$ | 3.88 s | 61.1 |

$^a$Values in parentheses are coupling constants in Hz.
Optical rotation (Compound P4) $[\alpha]\Delta$ − 12.53 (C = 0.06, MeOH) T = 21.0° C.

Figure 6:
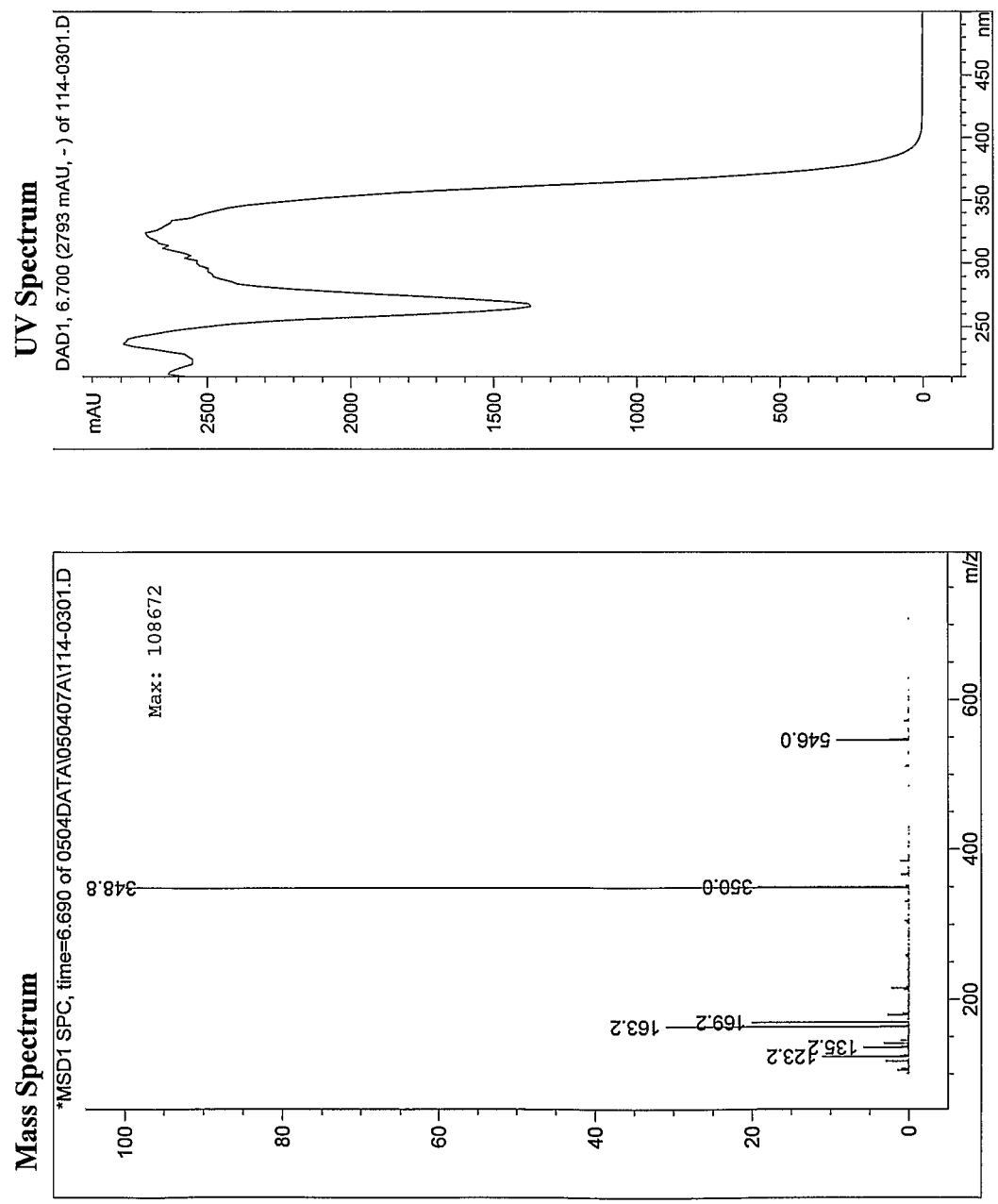
FIG. 6: UV and MS spectra for P6.
Figure 7:
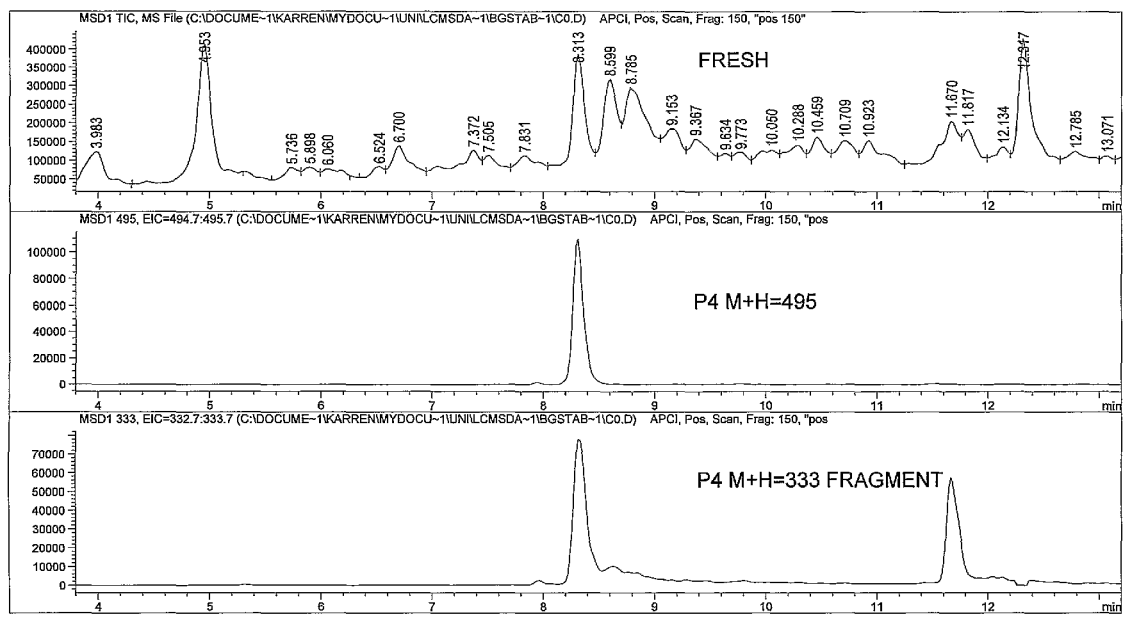
FIG. 7: MS data for P4 Glycosidase and Aglycone.

Compound 2 or P6 elutes at 8.7 minutes and is characterised by the EIC (Extracted Ion Chromatogram, FIG. 3) using m/z 546 (the parent ion plus H, M+H or M+1) as shown in FIG. 4B. Compound P6 showed a major fragment ion at m/Z 349 attributed to the loss of cinnamoyl ester and water. Chemical data for P6 are set out below, and NMR spectral data are set out in Table 5. UV and MS spectra for P6 are shown in FIG. 6.

| | |
|---|---|
| Chemical Name: | 4ξ,5ξ-di(3,4-dihydroxy-(E)-cinnamoyl)-2,6ξ-dihydroxyhept-2-en-1,7-dioic acid |
| Molecular Formula: | $C_{25}H_{22}O_{14}$ |
| Molecular Weight: | 546 |
| Optical Rotation, $[\alpha]_D$: | +23.5394 (Conc.: 0.3300 in methanol at 23.7° C.) |
| Chemical Structure: | 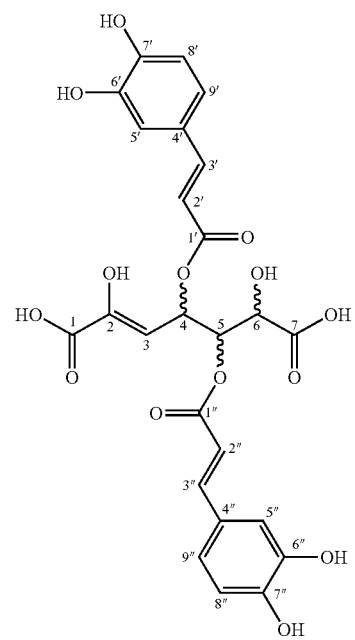 |

TABLE 5

$^1$H (500.13 MHz) and $^{13}$C (125.77 MHz)
NMR spectral data for P6 in methanol-$d_4$.

| Position C/H | $^1$H$^a$ | $^{13}$C |
|---|---|---|
| 1 | — | 164.8 |
| 2 | — | 146.1 |
| 3 | 6.02 dd (2.1, 1.8) | 109.3 |
| 4 | 5.98, m | 65.3 |
| 5 | 5.98, m | 66.4 |
| 6 | 5.14, s | 76.4 |
| 7 | — | 170.2 |
| 1'/1" | — | 167.9/168.0 |
| 2'/2" | 6.31, d (15.9)/6.16, d (15.9) | 114.1/114.3 |
| 3'/3" | 7.49, d (15.9)/7.53, d (15.9) | 148.1/148.6 |
| 4'/4" | — | 127.7/127.7 |
| 5'/5" | 6.99 d (2.1 )/7.03, d (2.1) | 115.1/115.4 |
| 6'/6" | — | 147.0/147.0 |
| 7'/7" | — | 149.9/150.0 |
| 8'/8" | 6.69 d (8.2)/6.76 d (8.2) | 116.6/116.7 |
| 9'/9" | 6.91 dd (2.1, 8.2)/6.81 dd (2.1, 8.2) | 123.6/123.7 |

$^a$Values in parentheses are coupling constants in Hz.
Optical rotation (Compound P6) [α]∆ + 46.24 (C = 0.375, MeOH) T = 21.5° C.

EXAMPLE 4

Antioxidant and Anti-inflammatory Activity of Active Constituents.

The antioxidant activity in the plant material was measured using the ORAC assay and the trolox equivalent value TE/g dried extract was determined. The highest activity was found in the non-sonicated extract of *C. cunninghamii* (C) with a TE/g of 7404. The extracts showed decreased antioxidant activity when sonicated.

The anti-inflammatory assay performed measured the level of prostaglandin $PGE_2$. The fresh *C. cunninghamii* extracts, both non-sonicated and sonicated, showed a strong dose response effect and possessed a higher inhibition of $PGE_2$ production than the positive control aspirin. The $IC_{50}$ value of sonicated extract was 0.097 mg/mL and the $IC_{50}$ of non-sonicated extract was 0.105 mg/mL. The results of these assays are set out in Tables 6 and 7 below.

TABLE 6

Inhibition of $PGE_2$ production of *Centipeda* fractions.

| Sample | Concentration of sample (mg/mL) | % inhibition of $PGE_2$ production ± SEM |
|---|---|---|
| E1 | 0.125 | 72.04 ± 5.50 |
| E2 | 0.0625 | 75.51 ± 6.90 |
| E3 | 0.125 | 76.33 ± 2.61 |
| E4 | 0.0625 | 94.29 ± 0.74 |
| E5 | 0.0625 | −26.94 ± 28.07 |
| E6 | 0.125 | 70.61 ± 4.08 |
| E7 | 0.0625 | 80.10 ± 7.04 |
| P4 | 0.125 | 67.76 ± 2.86 |
| P6 | 0.0625 | 74.49 ± 8.06 |
| Aspirin | 0.01 mM | 57.35 ± 14.42 |

Samples were tested for their ability to inhibit prostaglandin $E_2$ production in cells stimulated by a calcium ionophore, compared to stimulated cells not exposed to any sample. Inhibition was tested over a range of 3 concentrations, although a dose response was not observed for most samples. This is probably because the samples are very efficient at inhibiting $PGE_2$ production and the range of concentrations used was too narrow. The data presented are the maximal inhibition of $PGE_2$ observed for a given sample.

TABLE 7

Antioxidant capacity of *Centipeda* fractions.

| Sample | ORAC value (µmol TE/g of extract) |
|---|---|
| E1 | −772.3 |
| E2 | 2425.9 |
| E3 | 3941.1 |
| E4 | 829.2 |
| E5 | −1406.7 |
| E6 | −27.5 |
| E7 | −2089.8 |
| P4 | 3871.9 |
| P6 | 3415.1 |

The antioxidant capacity of the *Centipeda* fractions was measured using the ORAC procedure (Oxygen Radical Absorbance Capacity). A water soluble analogue of vitamin E, Trolox, was used as a reference standard, and the ORAC value is expressed as µmol of trolox equivalence (TE) per gram of sample extract.

EXAMPLE 5

5.1 Methods

Preparative HPLC was used to fractionate the crude extracts of *C. cunninghamii* into 30 or more fractions in a precise and repeatable manner. Fractionation of extracts was performed on a Gilson Preparative HPLC system employing a Gilson 322 binary pump system, a Gilson 156 UV-Vis dual wavelength detector and Gilson fraction collector (FC204). Separation was done by gradient elution with varying compositions of acetonitrile (solvent B) and water (solvent A). The prep HPLC operation is software driven using Gilson Unipoint v.3.0, and the details of the program and gradient timetable for the methods used for each extract is given below. The fractions were dried using a Rotary Evaporator Centrifuge (RVC) and combined as appropriate after verification by LCMS.

5.1.1 Initial Fractionation of Crude Extract.

Mobile Phase Gradient Timetable KB10-95 and BI10-95. Method:

| Time (min) | % A | % B | Flow Rate (mL/min) |
|---|---|---|---|
| 0 | 90 | 10 | 15.0 |
| 25 | 10 | 90 | 15.0 |
| 28 | 10 | 90 | 15.0 |
| 30 | 90 | 10 | 15.0 |
| 35 | 90 | 10 | 15.0 |

5.1.2 Sub-fractionation of *C. cunninghamii* Fraction 2.

Mobile Phase Gradient Timetable BI10-25. Method:

| Time (min) | % A | % B | Flow Rate (mL/min) |
|---|---|---|---|
| 0 | 90 | 10 | 15 |
| 15 | 75 | 25 | 15 |
| 18 | 90 | 10 | 15 |
| 20 | 90 | 10 | 15 |

5.1.3 Sub-fractionation of *C. cunninghamii* Fraction 11 and 14.

Mobile Phase Gradient Timetable B120-40. Method:

| Time (min) | % A | % B | Flow Rate (mL/min) |
|---|---|---|---|
| 0 | 80 | 20 | 15 |
| 15 | 60 | 40 | 15 |
| 18 | 80 | 20 | 15 |
| 20 | 80 | 20 | 15 |

5.1.4 Sub-fractionation of *C. cunninghamii* Fraction 16 and 17.

Mobile Phase Gradient Timetable KB20-50. Method:

| Time (min) | % A | % B | Flow Rate (mL/min) |
|---|---|---|---|
| 0 | 80 | 20 | 15 |
| 15 | 50 | 50 | 15 |
| 16 | 5 | 95 | 15 |
| 20 | 5 | 95 | 15 |
| 21 | 20 | 20 | 15 |
| 23 | 20 | 20 | 15 |

5.1.5 Fractionation of *C. cunninghamii* Flowers Ethanol Partition.

Mobile Phase Gradient Timetable KB20-60. Method:

| Time (min) | % A | % B | Flow Rate (mL/min) |
|---|---|---|---|
| 0 | 80 | 20 | 15 |
| 20 | 40 | 60 | 15 |
| 23 | 40 | 60 | 15 |
| 25 | 80 | 20 | 15 |
| 28 | 80 | 20 | 15 |

5.1.6 Fractionation of *C. cunninghamii* Flowers Hexane Partition.

Mobile Phase Gradient Timetable KB50-80. Method:

| Time (min) | % A | % B | Flow Rate (mL/min) |
|---|---|---|---|
| 0 | 60 | 40 | 15 |
| 16.4 | 25 | 75 | 15 |
| 20 | 25 | 75 | 15 |
| 21 | 10 | 90 | 15 |
| 28 | 10 | 90 | 15 |
| 30 | 60 | 40 | 15 |
| 33 | 60 | 40 | 15 |

5.2 Solid Phase Extraction (SPE)

SPE cartridges were used to rapidly partition the bulk of the crude plant extract into four fractions. Supelco, 60 mL SPE columns packed with 10 grams of Supelclean LC-18 were used. The 10 grams of sorbent generates a bed volume (BV) of 20 mL and a maximum sample loading capacity of 500 mg. SPE columns were first pre-wet with 6-10BV of methanol and then preconditioned using 6-10 BV of water. 500 mg of the extract was first dissolved in 1 BV of the starting mobile phase and loaded onto the SPE column. The sample was then eluted under gravity using:

| Fraction | Solvent | Volume |
|---|---|---|
| 1 | 100% Water | 60 mL |
| 2 | 20% ACN/Water | 60 mL |
| 3 | 40% ACN/Water | 60 mL |
| 4 | 100% ACN | 60 mL |

5.3 Pharmacology

5.3.1 Sample Preparation

The extracts were stored at 4° C. prior to analysis. The extracts were re-solubilised in solvent by sonicating for 20 minutes.

5.3.2 Oxygen Radical Absorbance Capacity (ORAC)

The ORAC assay employed in this study measured the antioxidant scavenging activity in the test samples, against peroxyl radicals induced by 2,2'-azobis(2-amidinopropane) dihydrochloride (AAPH) at 37° C. Fluorescein was used as the fluorescent probe. The method used is based on that of Huang et al.[1], Huang et al.[2] and Prior et al.[3]

[1] Huang et al., 2002. Journal of Agricultural and Food Chemistry 50(16): 1815-1821.
[2] Huang et al., 2002. Journal of Agricultural and Food Chemistry 50(16): 4437-4444.
[3] Prior et al., 2003. Journal of Agricultural and Food Chemistry 51(11): 3273-3279.

All samples were assayed using the hydrophilic ORAC procedure in serial dilution×4 with acetone:water:acetic acid; 70:29.5:0.5 (A:W:A,) and in quadruplicate, starting with the concentration relevant to the sample, depending on the approximated antioxidant capacity from an initial screen.

Trolox, a water soluble analogue of vitamin E, was used as a reference standard. A trolox standard curve was established from trolox standards prepared at 100, 50, 25, and 12.5 µM in A:W:A.

Briefly, 10 µL fluorescein ($6.0 \times 10^{-7}$ M), 20 µL samples/standards/control/blank (A:W:A) and 170 µL MPH (20 mM) were added per well. Immediately after loading, the plate was transferred to the plate reader preset to 37° C., and the fluorescence was measured 35 times at one minute intervals. The fluorescence readings were referenced to solvent blank wells. The final ORAC values were calculated using a regression equation between the Trolox concentration and the net area under the fluorescein decay curve, and where possible were expressed as Trolox equivalents (TE) as micromoles per gram of sample.

5.3.3 Inhibition of Prostaglandin $E_2$ Production

3T3 Swiss Albino fibroblast cell suspension (Phenol-red free DMEM with 10% FBS and 2 mM L-glutamine) was plated out into 96-well tissue culture plates ($1 \times 10^5$ cells/mL, 100 µL/well). The cells were cultured overnight at 37° C., 5% $CO_2$. The extracts and fractions were solubilised in DMSO, and diluted appropriately with media so the extracts were tested at a final concentration of 1000, 10, and 1 µg/mL; 5 µL of sample was added to each well. Cells+samples were incubated (37° C., 3 hours), before the addition of calcium ionophore A23187. Following 20 min incubation, the plate was centrifuged (1000 g, 3 min) and the supernatants were removed. Included on the plate was a positive control (aspirin; 100 µM), and DMSO control, both with and without calcium ionophore A23187.

The supernatants were diluted by serial dilution (1:500) in enzyme immunoassay (EIA) buffer, and assayed for $PGE_2$ using the Prostaglandin $E_2$ EIA Monoclonal Kit (Cayman Chemical; Cat No. 514010), according to manufacturers' instructions.

5.4 Isolation and Identification of Compounds Using Chromatography and Spectroscopy.

Figure 8:
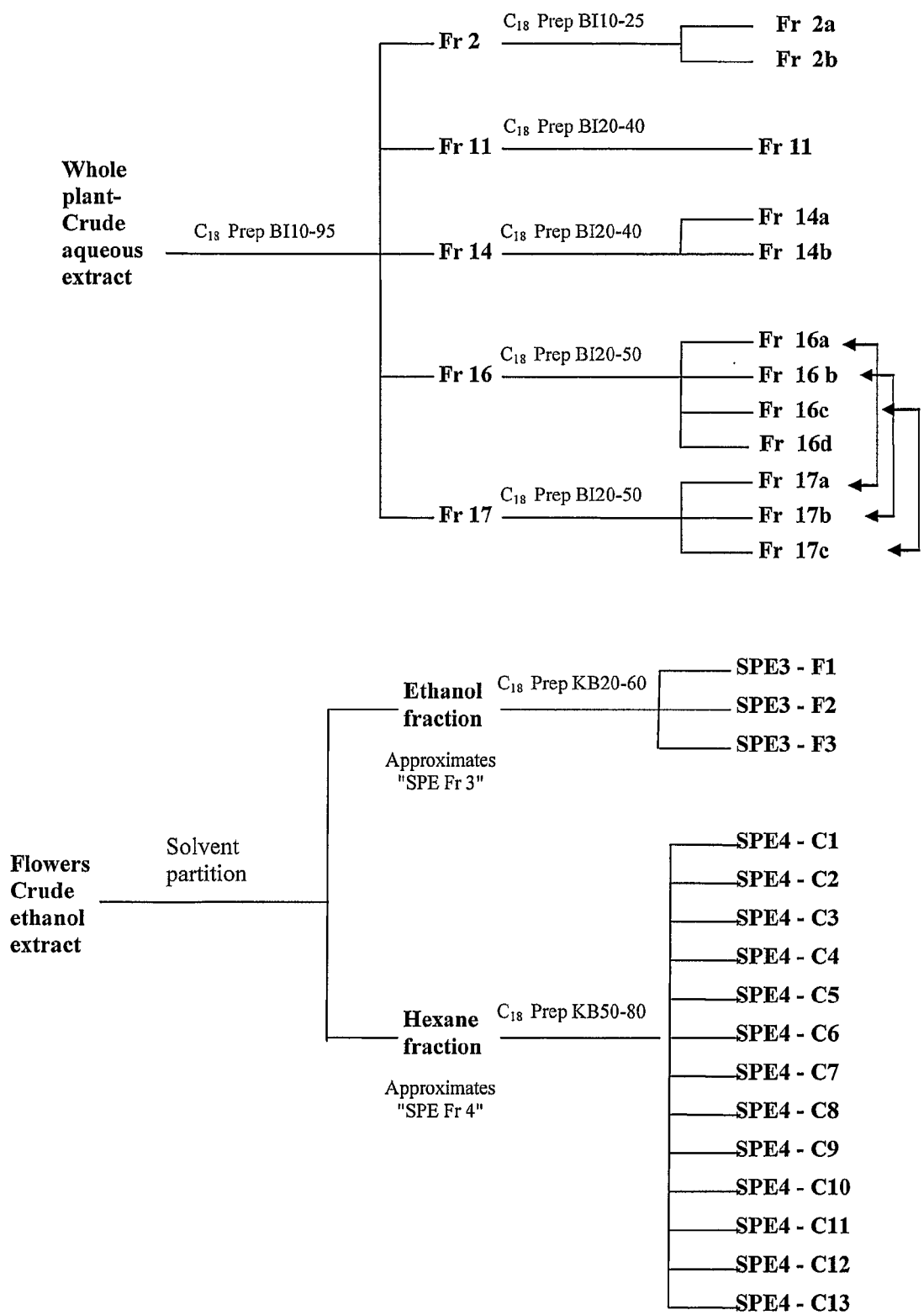
FIG. 8: Isolation scheme for anti-inflammatory and antioxidant compounds from *C. cunninghamii*.

An overview of the extraction techniques and preparative HPLC methods used to isolate pure compounds from *C. cunninghamii* is summarized in FIG. 8. To isolate the polar metabolites a fresh aqueous extract of *C. cunninghamii* was prepared just prior to fractionation, and the extract was fractionated by reverse phase preparative HPLC using the BI(10-95) method outlined above. It was necessary to sub-fractionate fractions; 2, 11, 14, 16 and 17 using the mobile phase gradients as indicated in FIG. 8 to obtain pure compounds. Nine compounds have been isolated from the aqueous extract as shown in FIG. 8. Two of these compounds, fractions 11 (Compound 1, flavonoid glycoside) and 16a (Compound 2), had been previously isolated and their identities were confirmed by their $^1$H and $^{13}$C NMR spectra.

Fractions 16b/17b (Compound 8), 16c/17c (Compound 9) and 16d (Compound 10) showed similar $^1$H NMR profiles with fraction 16a/17a (Compound 2, from previous structural elucidation work) except that additional proton signals were observed in Compounds 8, 9 and 10 that each integrated to 3 protons. This strongly suggested that Compounds 8, 9 and 10 are methyl esters of Compound 2 and HMBC data confirmed that Compound 8 was methylated at the 7-COOH position, Compound 9 was methylated at the 1-COOH position and Compound 10 was methylated at both the 1- and 7-COOH positions as shown in their structures below. The NMR spectral data of these compounds (2, 8, 9 and 10) are summarised in Tables 8 and 9.

Figure 9:
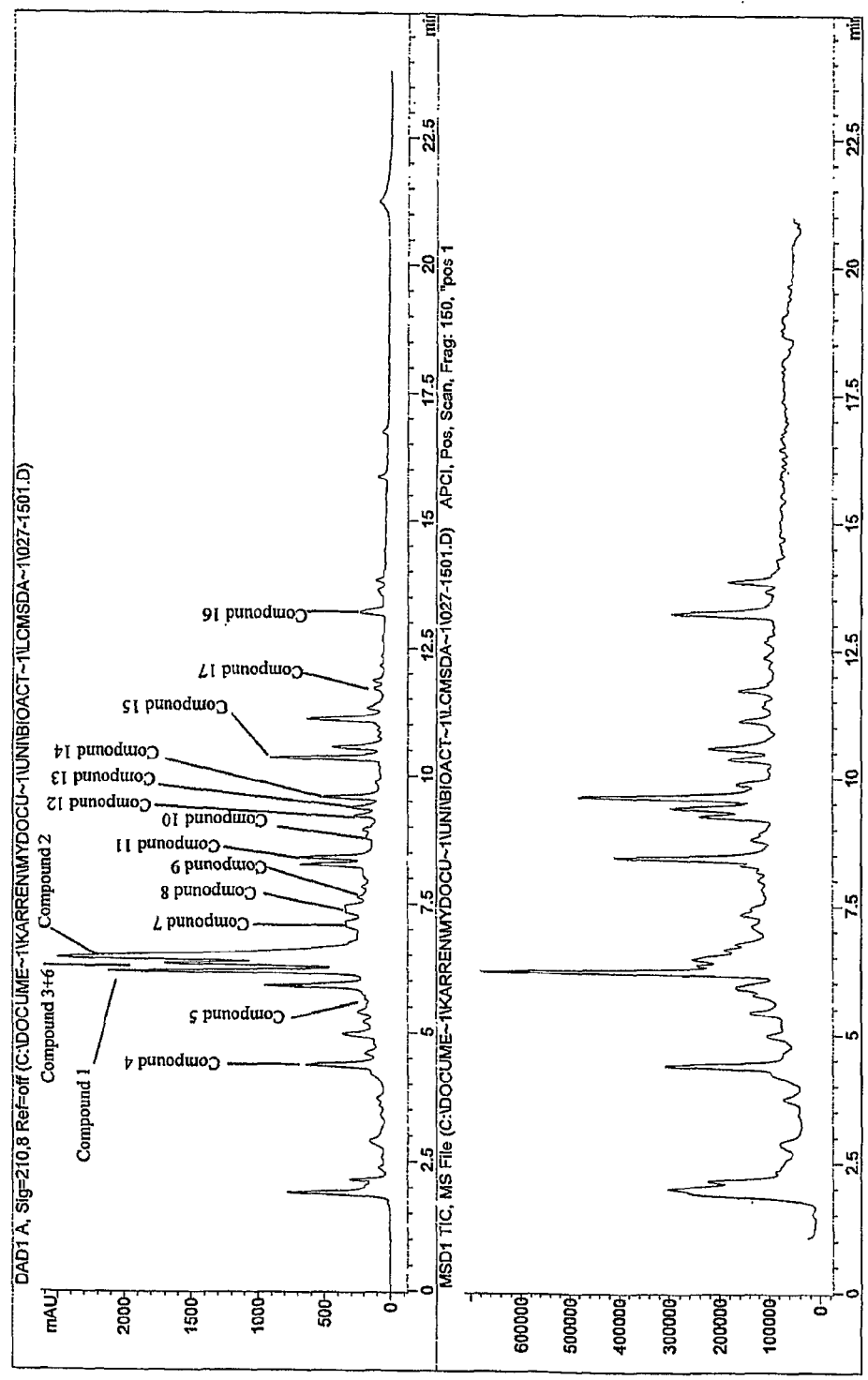
FIG. 9: Compounds isolated from *C. cunninghamii*.

From the results of the bioassay guided fractionation it was observed that the bulk of the anti-inflammatory activity occurs in the region 7-15 minutes in the chromatogram (FIG. 9) with these compounds only present in small quantities. These metabolites predominate in the flowers and are present at quite low concentrations. An enriched extract containing these compounds was produced by sieving the flower heads (very fine petals) from the rest of the plant material. During the initial stages of this isolation work C-18 Solid Phase Extraction (SPE) cartridges were used to rapidly partition the bulk of the crude plant extract into four fractions. SPE Fraction 3 and 4 contained the compounds of interest. It was necessary to adapt the isolation to a larger scale. The 100% aqueous extract described above approximates the SPE fractions 1 & 2. SPE fraction 3 and 4 were approximated by extracting with 100% ethanol followed by an ethanol/hexane solvent partition. The ethanol extract of the flowers was back-extracted with hexane to afford the non-polar compounds. The hexane (approximately SPE Fr 4) and the ethanol partitions (approximately SPE Fr 3) were then evaporated to dryness and subjected to RP-prep HPLC to attain pure compounds. All of the compounds isolated using this scheme are indicated on the chromatogram in FIG. 9.

The compounds obtained from the ethanol partition (FIG. 8) were all identified. SPE3-Fraction 1 (Compound 11) was elucidated as the flavone axillarin and the $^1$H and $^{13}$C NMR data are summarised in Table 10. SPE3-fractions 2a (Compound 12), 2b (Compound 13) and 3 (Compound 14) were all deduced to be methoxy derivatives of 4',5,7-trihydroxy flavones and these were identified as isokaempferide, 4',5,7-trihydroxy-3,6-dimethoxy-flavone and jaceidin, respectively. The structures of these compounds are shown below and the $^1$H and $^{13}$C NMR spectral data are also summarised in Table 10.

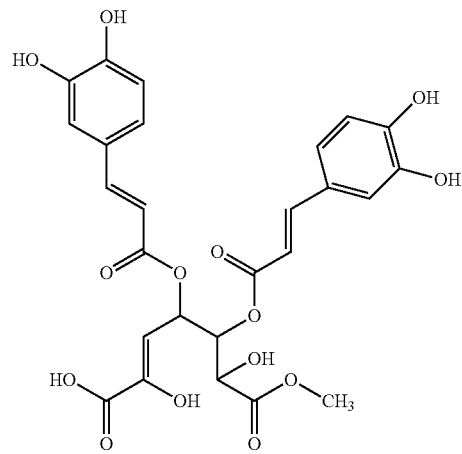

Compound 8

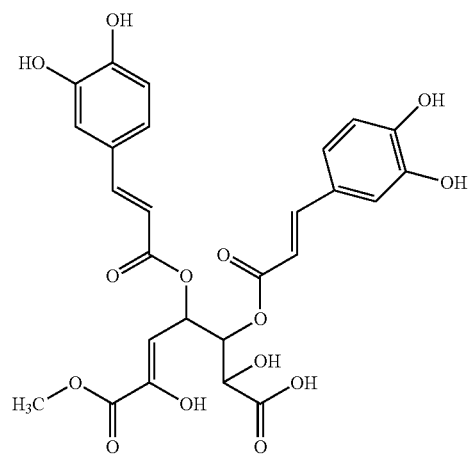

Compound 9

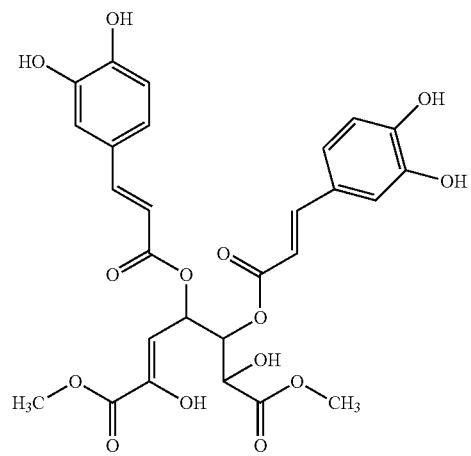

Compound 10

-continued

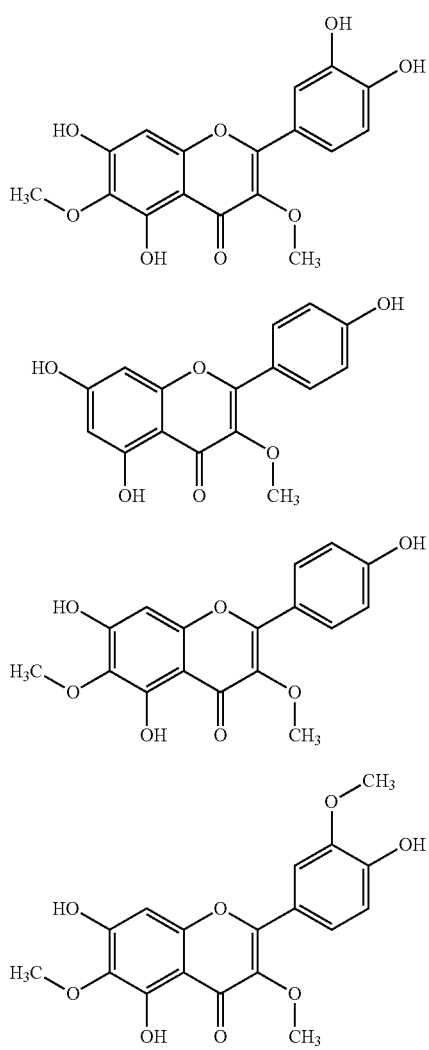

Compound 11

Compound 12

Compound 13

Compound 14

TABLE 8

$^1$H and $^{13}$C NMR spectral data for compounds 2 and 8 in methanol-$d_4$.

| | Chemical Shift, ppm | | | |
|---|---|---|---|---|
| | Compound 2 | | Compound 8 | |
| Position | $^1$H | $^{13}$C | $^1$H | $^{13}$C |
| 1 | — | 164.8 | — | 164.4 |
| 2 | — | 146.1 | — | 146.3 |
| 3 | 6.02, dd (1.9, 2.2) | 109.3 | 6.03, dd (1.6, 2.1) | 109.1 |
| 4 | 5.97, m | 65.4$^a$ | 5.93, m | 66.0 |
| 5 | 5.98, m | 66.3$^a$ | 5.89, m | 65.4 |
| 6 | 5.14, m | 76.3 | 5.18, br s | 76.0 |
| 7 | — | 170.1 | — | 168.9 |
| 7-COOMe | | | 3.79, s | 53.4 |
| 1'/1" | — | 168.0/167.9 | — | 167.9/167.9 |
| 2'/2" | 6.30, d (15.9)/ 6.16, d (15.9) | 114.1/114.3 | 6.29, d (15.9)/ 6.17, d (15.9) | 148.7/148.2 |
| 3'/3" | 7.54 d (15.9)/ 7.50 d (15.9) | 148.6/148.1 | 7.54 d (15.9)/ 7.50 d (15.9) | 148.7/148.2 |
| 4'/4" | — | 128.0/128.1 | — | 127.6/127.7 |
| 5'/5" | 7.03, d (2.0)/ 6.99, d (2.0) | 115.4/115.3 | 7.04, d (2.0)/ 7.00, d (2.0) | 115.4/115.1 |

TABLE 8-continued $^1$H and $^{13}$C NMR spectral data for compounds 2 and 8 in methanol-$d_4$.

| | Chemical Shift, ppm | | | |
|---|---|---|---|---|
| | Compound 2 | | Compound 8 | |
| Position | $^1$H | $^{13}$C | $^1$H | $^{13}$C |
| 6'/6" | — | 147.0/147.0 | — | 147.0/147.0 |
| 7'/7" | — | 150.1/150.0 | — | 150.1/150.0 |
| 8'/8" | 6.76, d (8.2)/ 6.69, d (8.2) | 116.7/116.6 | 6.76, d (8.2)/ 6.69, d (8.2) | 116.7/116.6 |
| 9'/9" | 6.91, dd (2.0, 8.2)/6.81, dd (2.0, 8.2) | 123.6/123.7 | 6.91, dd (2.0, 8.2)/6.82, dd (2.0, 8.2) | 123.6/123.7 |

Optical Rotation data;

Compound 2 [α]Δ + 46.24 (C = 0.375, MeOH) T = 21.5° C.

Compound 8 [α]Δ + 20.62 (C = 0.24, MeOH) T = 21.8° C.

TABLE 9

$^1$H and $^{13}$C NMR spectral data for compounds 9 and 10 in methanol-$d_4$.

| | Chemical Shift, ppm | | | |
|---|---|---|---|---|
| | Compound 9 | | Compound 10 | |
| Position | $^1$H | $^{13}$C | $^1$H | $^{13}$C |
| 1 | — | 1636.8 | — | 163.4 |
| 2 | — | 145.9 | — | 145.9 |
| 3 | 6.01, dd (1.8, 2.2) | 109.9 | 6.03, dd (1.6, 2.6) | 109.3 |
| 4 | 5.98-5.95, m$^a$ | 66.3$^b$ | 5.95, m | 66.0 |
| 5 | 5.98-5.95, m$^a$ | 65.4$^b$ | 5.89, ddd (1.6, 1.7, 4.6) | 65.4 |
| 6 | 5.118, br s | 76.3 | 5.18, br s | 76.1 |
| 7 | — | 169.9 | — | 168.8 |
| 1-COOMe | 3.86, s | 53.2 | 3.85, s | 53.2 |
| 7-COOMe | | | 3.79, s | 53.4 |
| 1'/1" | — | 168.0/167.9 | — | 167.9/167.9 |
| 2'/2" | 6.29, d (15.9)/ 6.16, d (15.9) | 114.1/114.3 | 6.27, d (16.0)/ 6.69, d (16.0) | 113.9/114.2 |
| 3'/3" | 7.53 d (15.9)/ 7.49 d (15.9) | 148.6/148.1 | 7.53 d (16.09)/ 7.50 d (16.0) | 148.7/148.2 |
| 4'/4" | — | 127.7/127.7 | — | 127.7/127.7 |
| 5'/5" | 7.03, d (2.0)/ 6.99, d (2.0) | 115.3/115.1 | 7.03, d (2.0)/ 6.99, d (2.0) | 115.4/115.1 |
| 6'/6" | — | 147.0/147.0 | — | 147.0/147.0 |
| 7'/7" | — | 150.1/150.0 | — | 150.1/150.0 |
| 8'/8" | 6.76, d (8.2)/ 6.69, d (8.2) | 116.7/116.6 | 6.76, d (8.2)/ 6.69, d (8.2) | 116.7/116.6 |
| 9'/9" | 6.91, dd (2.0, 8.2)/6.81, dd (2.0, 8.2) | 123.7/123.6 | 6.91, dd (2.0, 8.2)/6.82, dd (2.0, 8.2) | 123.6/123.7 |

$^a$Overlapping peaks.

Optical Rotation data;

Compound 9 [α]Δ + 22.58 (C = 0.11, MeOH) T = 22.1° C.

Compound 10 [α] Δ + 29.09 (C = 0.395, MeOH) T = 22.2° C.

TABLE 10

$^1$H and $^{13}$C NMR spectral data for compounds 11, 12, 13 and 14 in methanol-$d_4$.

| | Compound 11 | | Compound 12 | | Compound 13 | | Compound 14 | |
|---|---|---|---|---|---|---|---|---|
| Position | $^1$H | $^{13}$C | $^1$H | $^{13}$C | $^1$H | $^{13}$C | $^1$H | $^{13}$C |
| 1 | — | — | — | — | — | — | — | — |
| 2 | — | 158.3 | — | 158.2 | — | 158.2 | — | 158.1 |
| 3 | — | 139.4 | — | 139.5 | — | 139.5 | — | 139.5 |
| 4 | — | 180.5 | — | 180.2 | — | 180.5 | — | 180.5 |
| 5 | — | 154.0 | — | 163.3 | — | 158.3 | — | 153.9 |
| 6 | — | 132.7 | 6.40, d (2.1) | 100.0 | — | 132.6 | — | 132.8 |
| 7 | — | 158.9 | — | 166.2 | — | 154.0 | — | 158.9 |
| 8 | 6.50, s | 95.1 | 6.20, d (2.1) | 94.9 | 6.52, s | 95.2 | 6.53, s | 95.2 |
| 9 | — | 153.9 | — | 158.6 | — | 159.1 | — | 153.7 |
| 10 | — | 106.5 | — | 106.1 | — | 106.5 | — | 106.5 |
| 3-OCH$_3$ | 3.79, s | 60.5 | 3.78, s | 60.7 | 3.78, s | 60.7 | 3.80, s | 60.8 |
| 6-OCH$_3$ | 3.88, s | 61.1 | | | 3.88, s | 61.1 | 3.88, s | 61.1 |
| 1' | — | 123.1 | — | 122.8 | — | 122.8 | — | 123.1 |
| 2' | 7.62, d (2.2) | 116.7$^a$ | 7.98, d (8.9) | 131.6 | 7.98, d (8.9) | 131.6 | 7.71, d (2.0) | 113.1 |
| 3' | — | 146.6 | 6.92, d (8.9) | 116.6 | 6.92, d (8.9) | 116.6 | — | 149.1 |
| 4' | — | 150.1 | — | 161.9 | — | 161.9 | — | 151.3 |
| 5' | 6.89, d (8.5) | 116.6$^a$ | 6.92, d (8.9) | 116.6 | 6.92, d (8.0) | 116.6 | 6.94, d (8.4) | 116.0 |
| 6' | 7.53, dd (2.2, 8.5) | 122.5 | 7.98, d (8.9) | 131.6 | 7.98, d (8.0) | 131.6 | 7.63, dd (2.0, 8.4) | 123.9 |
| 3'-OCH$_3$ | | | | | | | 3.94, s | 56.7 |

$^a$Values could be interchangeable.

5.5 Anti-inflammatory and Antioxidant Activity.

A sub-sample of each of the pure compounds indicated above was submitted to the ORAC and PGE$_2$ bioassays to evaluate their antioxidant and anti-inflammatory potential.

The compounds were tested at a concentration of 5.0 µg/mL in the PGE$_2$ assay. The results of the assay are presented in Table 11. The anti-inflammatory results for aspirin were at the expected levels. It was observed that all of the test samples were completely soluble at this concentration. The samples were also tested for their antiinflammatory potential over a range of concentrations in order to determine their IC 50 values. The IC 50 values for selected compounds are given below in Table 12.

TABLE 11

Anti-inflammatory capacity of *Centipeda cunninghamii* compounds (5.0 µg/mL).

| Compound | Sample | Average | Std. dev. |
|---|---|---|---|
| Compound 1 | 11 | 52.2 | 0.91 |
| Compound 2 | 16a | 67.38 | 4.73 |
| Compound 8 | 16b | 73.50 | 4.08 |
| Compound 9 | 16c | 45.00 | 8.94 |
| Compound 10 | 16d | 73.95 | 2.52 |
| | Aspirin 100 µM | 54.6 | 10.6 |

From the results of this assay it was observed that all of the compounds tested are more potent than aspirin in inhibiting PGE$_2$.

TABLE 12

IC 50 values for *C. cunninghamii* compounds.

| Compound | Sample | Average | Std. dev. |
|---|---|---|---|
| Compound 1 | 11 | 1.47 | 0.75 |
| Compound 2 | 16a | 2.48 | 0.83 |
| Compound 8 | 16b | 4.73 | 0.93 |

Compounds 9 and 10, over the concentration range tested, did not exhibit a standard dose response type curve and hence the IC50 values could not be calculated.

Results from the ORAC assay (Table 13) show that the compounds tested all exhibited very high antioxidant potential. For comparison, the antioxidant capacity of green tea extract has been found to be 7108 TE/gram.

TABLE 13

Antioxidant capacity of *Centipeda cunninghamii* compounds

| Compound | Sample | TE/g extract | ±SD |
|---|---|---|---|
| Compound 1 | Fr 11 | 12178 | 942 |
| Compound 2 | Fr 16a | 13781 | 828 |
| Compound 8 | Fr 16b | 8122 | 272 |
| Compound 9 | Fr 16c | 6822 | 361 |
| Compound 10 | Fr 16d | 3957 | 69 |

What is claimed is:

1. An isolated compound of Formula II:

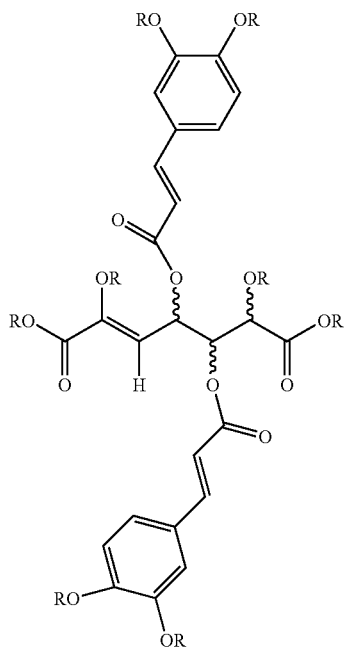

(II)

wherein each R, which may be the same or different, is selected from the group consisting of hydrogen and $R_1$; and each $R_1$, which may be the same or different, is selected from the group consisting of substituted or unsubstituted alkyl, substituted or unsubstituted cycloalkyl, substituted or unsubstituted cycloalkylalkyl, substituted or unsubstituted aryl, substituted or unsubstituted arylalkyl, a protecting group, —C(O)—$R^a$, —C(O)O—$R^a$, —C(O)NR$^a$R$^a$, —S(O)$_n$—NR$^a$R$^a$ (wherein n represents 1 or 2, and $R^a$ is selected from the group consisting of hydrogen and substituted or unsubstituted alkyl); and their pharmaceutically acceptable salts.

2. A compound according to claim 1, wherein R is hydrogen or alkyl.

3. A compound selected from:
 i. 4ξ,5ξ-Di-O-caffeoyl-2,6ξ-dihydroxyhept-2-en-1,7-dioic acid (Compound 2)
 ii. 4ξ,5ξ-Di-O-caffeoyl-2,6ξ-dihydrodyhept-2-en-1,7-dioic acid-7-methyl ester (Compound 8)
 iii. 4ξ,5ξ-Di-O-caffeoyl-2,6ξ-dihydroxyhept-2-en-1,7-dioic acid-1-methyl ester (Compound 9)
 iv. 4ξ,5ξ-Di-O-caffeoyl-2,6ξ-dihydroxyhept-2-en-1,7-dioic acid-dimethyl ester (Compound 10)
 in substantially purified form, and pharmaceutically acceptable salts thereof.

4. A method of antioxidant or anti-inflammatory treatment of a human or other mammal, which comprises administration to said human or other mammal a therapeutically effective amount of a compound according to claim 1, or a pharmaceutically acceptable salt thereof.

5. A pharmaceutical composition for antioxidant or anti-inflammatory treatment of a human or other mammal which comprises a compound according to claim 1, or a pharmaceutically acceptable salt thereof, together with one or more pharmaceutically acceptable carriers and/or diluents.

6. A method of antioxidant or anti-inflammatory treatment of a human or other mammal, which comprises administration to said human or other mammal a therapeutically effective amount of a compound according to claim 2, or a pharmaceutically acceptable salt thereof.

7. A method of antioxidant or anti-inflammatory treatment of a human or other mammal, which comprises administration to said human or other mammal a therapeutically effective amount of a compound according to claim 3, or a pharmaceutically acceptable salt thereof.

8. A pharmaceutical composition for antioxidant or anti-inflammatory treatment of a human or other mammal which comprises a compound according to claim 2, or a pharmaceutically acceptable salt thereof, together with one or more pharmaceutically acceptable carriers and/or diluents.

9. A pharmaceutical composition for antioxidant or anti-inflammatory treatment of a human or other mammal which comprises a compound according to claim 3, or a pharmaceutically acceptable salt thereof, together with one or more pharmaceutically acceptable carriers and/or diluents.

10. A pharmaceutical composition according to claim 5, wherein the composition further comprises a compound of Formula I:

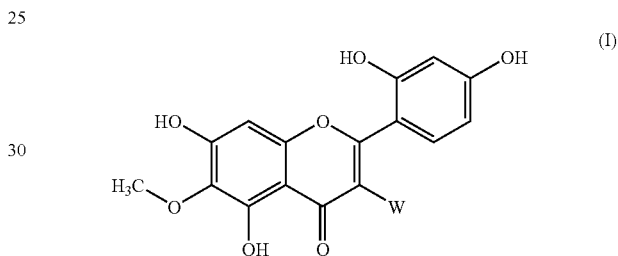

(I)

wherein W is a monosaccharide group selected from pentose and hexose sugars in pyranose or furanose form, a substituted monosaccharide group in which one or more of the —OH groups of a said pentose or hexose sugar is replaced by —OR$_1$ group or a disaccharide group comprising two of said monosaccharide or substituted monosaccharide groups linked by a glycosidic bond;

wherein $R_1$ is selected from the group consisting of substituted or unsubstituted alkyl, substituted or unsubstituted cycloalkyl, substituted or unsubstituted cycloalkylalkyl, substituted or unsubstituted aryl, substituted or unsubstituted arylalkyl, a protecting group, —C(O)—$R^a$, —C(O)O—$R^a$, —C(O)NR$^a$R$^a$—, —S(O)$_n$, —$R^a$ and —S(O)$_n$—NR$^a$R$^a$ (wherein n represents 1 or 2, and $R^a$ is selected from the group consisting of hydrogen and substituted or unsubstituted alkyl); and their pharmaceutically acceptable salts.

11. A pharmaceutical composition according to claim 10, wherein in Formula I, W is a β-D-glucopyranoside group of Formula III:

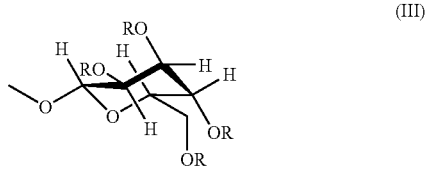

(III)

wherein each R, which may be the same or different, is selected from the group consisting of hydrogen and $R_1$;

and each $R_1$ which may be the same or different is selected from the group consisting of substituted or unsubstituted alkyl, substituted or unsubstituted cycloalkyl, substituted or unsubstituted cycloalkylalkyl, substituted or unsubstituted aryl, substituted or unsubstituted arylalkyl, a protecting group, —C(O)—$R^a$, —C(O)O—$R^a$, —C(O)N$R^a R^a$—, —S(O)$_n$—$R^a$ and —S(O)$_n$—N$R^a R^a$ (wherein n represents 1 or 2, and $R^a$ is selected from the group consisting of hydrogen and substituted or unsubstituted alkyl); and their pharmaceutically acceptable salts.

\* \* \* \* \*